(12) United States Patent
Behrendt et al.

(10) Patent No.: US 11,086,029 B2
(45) Date of Patent: Aug. 10, 2021

(54) APPARATUS FOR OPTICALLY CAPTURING A SCREEN

(71) Applicant: Fraunhofer-Gesellschaft zur Foerderung der angewandten Forschung e.V., Munich (DE)

(72) Inventors: Rolf Behrendt, Dormitz (DE); Wolfgang Groeger, Roettenbach (DE); Peter Schmitt, Erlangen (DE); Andreas Jobst, Nuremberg (DE); Guenther Kostka, Erlangen (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 172 days.

(21) Appl. No.: 16/160,901

(22) Filed: Oct. 15, 2018

(65) Prior Publication Data

US 2019/0049596 A1    Feb. 14, 2019

Related U.S. Application Data

(63) Continuation of application No. PCT/EP2017/058103, filed on Apr. 5, 2017.

(30) Foreign Application Priority Data

Apr. 15, 2016   (DE) .................. 10 2016 206 444.4

(51) Int. Cl.
*G01T 1/20*    (2006.01)
*G03B 27/72*   (2006.01)
*G01N 23/046*  (2018.01)
*H04N 5/32*    (2006.01)
*G03B 42/02*   (2021.01)
(Continued)

(52) U.S. Cl.
CPC .......... *G01T 1/2002* (2013.01); *G01N 23/04* (2013.01); *G01N 23/046* (2013.01); *G03B 27/725* (2013.01); *G21F 3/00* (2013.01); *H04N 5/32* (2013.01); *G03B 42/02* (2013.01)

(58) Field of Classification Search
CPC .... G01T 1/2002; G01N 23/04; G01N 23/046; G03B 24/725; G21F 3/00; H04N 5/32
See application file for complete search history.

(56) References Cited

U.S. PATENT DOCUMENTS 3,897,250 A    7/1975  Weishaupt
4,492,869 A *  1/1985  Suzuki .................. G01T 1/2018
                                                          250/367

(Continued)

FOREIGN PATENT DOCUMENTS

CN    1493176 A    4/2004
CN   102959964 A   3/2013
(Continued)

*Primary Examiner* — David P Porta
*Assistant Examiner* — Jeremy S Valentiner
(74) *Attorney, Agent, or Firm* — Michael A. Glenn; Perkins Coie LLP (57) ABSTRACT

Embodiments provide image capturing apparatuses having a screen, a plurality of mirrors and a plurality of cameras. The plurality of mirrors and the plurality of cameras is arranged such that the plurality of cameras capture a portion of the screen via a respective one of the plurality of mirrors, wherein the plurality of cameras is arranged obliquely with respect to the screen.

24 Claims, 8 Drawing Sheets

(51) Int. Cl.
*G01N 23/04* (2018.01)
*G21F 3/00* (2006.01)

(56) References Cited

U.S. PATENT DOCUMENTS

| | | | |
|---|---|---|---|
| 5,790,629 A * | 8/1998 | Svensson | H04N 5/32 |
| | | | 378/98.7 |
| 6,038,286 A | 3/2000 | Wagli et al. | |
| 6,353,657 B1 * | 3/2002 | Bayrock | G01N 23/085 |
| | | | 378/98.3 |
| 2003/0031300 A1 | 2/2003 | Cheng | |
| 2006/0023078 A1 * | 2/2006 | Schmitt | H04N 5/32 |
| | | | 348/222.1 |
| 2006/0133571 A1 * | 6/2006 | Winsor | G01T 1/362 |
| | | | 378/98.8 |
| 2009/0016490 A1 * | 1/2009 | Campbell | H04N 5/32 |
| | | | 378/98.3 |
| 2009/0196400 A1 * | 8/2009 | Schmitt | G01T 1/20 |
| | | | 378/145 |
| 2011/0128358 A1 * | 6/2011 | Cannon | G01T 1/20 |
| | | | 348/61 |
| 2013/0044181 A1 | 2/2013 | Baker et al. | |
| 2014/0064458 A1 | 3/2014 | Jobst et al. | |
| 2015/0206698 A1 | 7/2015 | Hori et al. | |
| 2016/0238719 A1 * | 8/2016 | Kataoka | G01T 1/244 |
| 2017/0146454 A1 | 5/2017 | Knox et al. | |

FOREIGN PATENT DOCUMENTS

| | | |
|---|---|---|
| CN | 104458777 A | 3/2015 |
| CN | 104584179 A | 4/2015 |
| CN | 104599431 A | 5/2015 |
| DE | 10301941 A1 | 8/2004 |
| DE | 102008007595 A1 | 8/2009 |
| DE | 102011075527 A1 | 11/2012 |
| DE | 102013104835 A1 | 12/2013 |
| EP | 0862748 B2 | 5/2006 |
| EP | 1870770 A1 | 12/2007 |
| JP | 2010253049 A | 11/2010 |
| WO | 2014000810 A1 | 1/2014 |

* cited by examiner

APPARATUS FOR OPTICALLY CAPTURING A SCREEN

CROSS-REFERENCE TO RELATED APPLICATIONS

This application is a continuation of copending International Application No. PCT/EP2017/058103, filed Apr. 5, 2017, which is incorporated herein by reference in its entirety, and additionally claims priority from German Application No. DE 10 2016 206 444.4, filed Apr. 15, 2016, which is incorporated herein by reference in its entirety.

BACKGROUND OF THE INVENTION

Embodiments of the present invention refer to an image capturing apparatus, and in particular to an image capturing apparatus for optically capturing a screen (e.g. a scintillator screen) with several cameras. Some embodiments refer to a radiation-protected X-ray camera that may be employed in digital radioscopy, e.g., for a quality control of products.

In industrial and medical radioscopy, so-called flat-panel detectors are currently advantageously used. With these, the X-radiation is usually converted via a scintillator screen into visible light and the same is detected via a semiconductor layer (amorphous or crystalline silicon) arranged directly behind the scintillator screen in the beam direction and is converted into an image. The efficiency of a scintillator screen depends, among other things, on the set energy of the X-ray quanta. The higher the energy of the X-radiation, the less X-ray quanta are absorbed in the scintillator and contribute to the image. The unabsorbed X-ray quanta may be absorbed by the underlying semiconductor layer, damaging the same. At an appropriate dose, this radiation damage ultimately leads to the failure of the detector.

Figure 1:
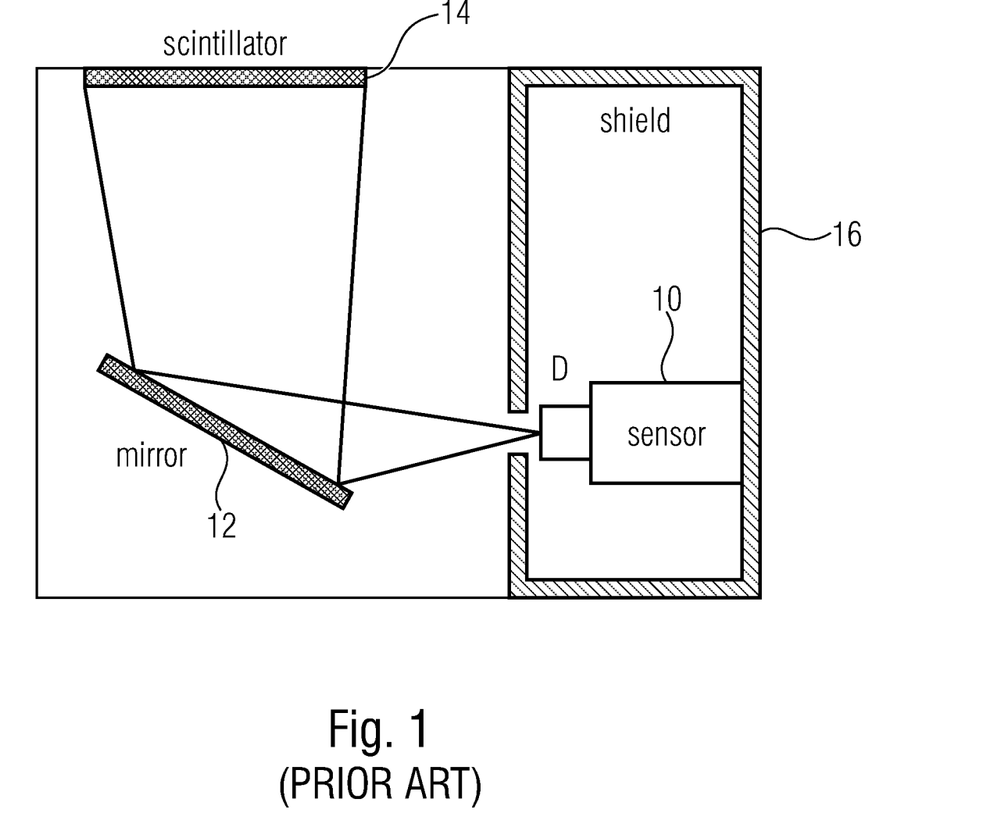
FIG. 1 shows a known mirror/camera arrangement in which a camera captures a scintillator via a mirror.

Furthermore, X-ray detectors are used in which the X-radiation is also first converted into visible light by a scintillator, however, the same is subsequently imaged by means of an image amplifier or optical imaging via an objective, e.g., onto CCD cameras or CMOS cameras directly or by means of a mirror, as is shown in FIG. 1.

In detail, FIG. 1 shows a mirror/camera arrangement in which a camera 10 captures a scintillator 14 via a mirror 12. The camera 10 is arranged with respect to the scintillator 14 such that a capturing direction of the camera (sensor) 10 extends in parallel to a scintillator plane. The camera 10 is surrounded by a shield 16 comprising an opening in an area adjacent to an objective of the camera 10.

In other words, FIG. 1 shows a simple single-row mirror/camera arrangement according to the conventional technology. Any number of cameras 10 may be arranged in rows perpendicular to the drawing plane.

Figure 2:
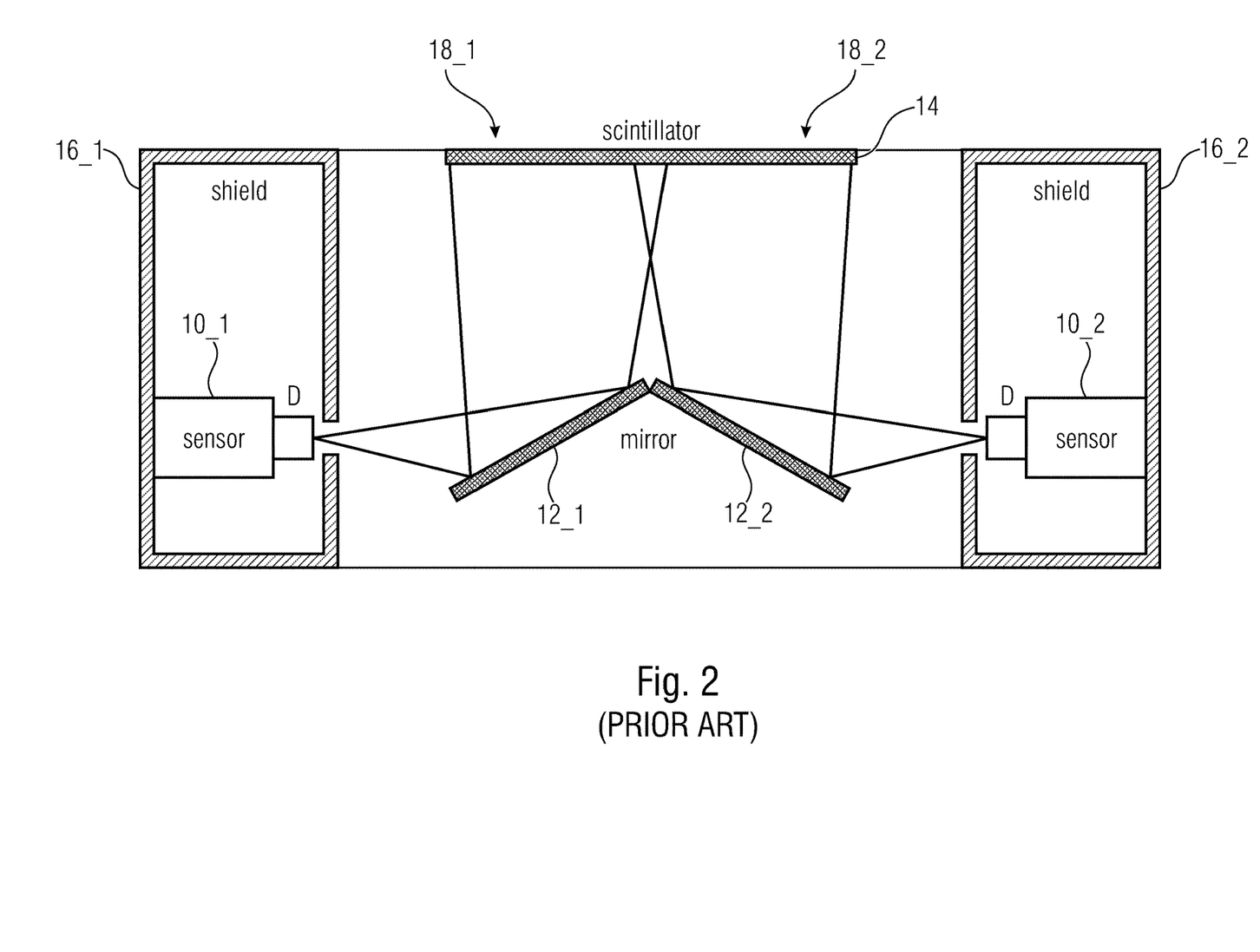
FIG. 2 shows a known mirror/camera arrangement in which two cameras each capture a portion of a scintillator via a respective mirror.

EP 0 862 748 describes an arrangement in which the visible light originating from the scintillator is deflected via V-shaped mirror arrangement such that the optical path behind the mirror is essentially parallel to the scintillator screen. By this, the radiation-sensitive cameras may be arranged outside the X-ray path and radiation damage may be avoided. FIG. 2 shows an example of an arrangement according to the conventional technology, wherein the V-shaped mirror arrangement of EP 0 862 748 is illustrated.

In the mirror/camera arrangement shown in FIG. 2, two cameras 10_1 and 10_2 capture a portion 18_1 and 18_2 of a scintillator 14 via a mirror 12_1 and 12_2, respectively. With respect to the scintillator 14, the cameras 10_1 and 10_2 are arranged such that capturing directions of the cameras 10_1 and 10_2 extend in parallel to a scintillator plane. Furthermore, the cameras 10_1 and 10_2 are each surrounded by a shield 16_1 and 16_2, respectively, comprising openings in areas adjacent to objectives of the respective cameras 10_1 and 10_2.

Thus, FIG. 2 shows a V-shaped mirror arrangement according to EP 0 862 748, or a two-row mirror/camera arrangement according to the conventional technology. Any number of cameras may be arranged in rows perpendicular to the drawing plane.

DE 103 01 941 describes an arrangement in which the visible light originating from the scintillator is deflected via two mirrors arranged in parallel and reaches the optical camera in this way. By periodically arranging this parallel mirror arrangement in a row, it is possible to image a scintillator surface of any size with a multitude of optical cameras.

Figure 3:
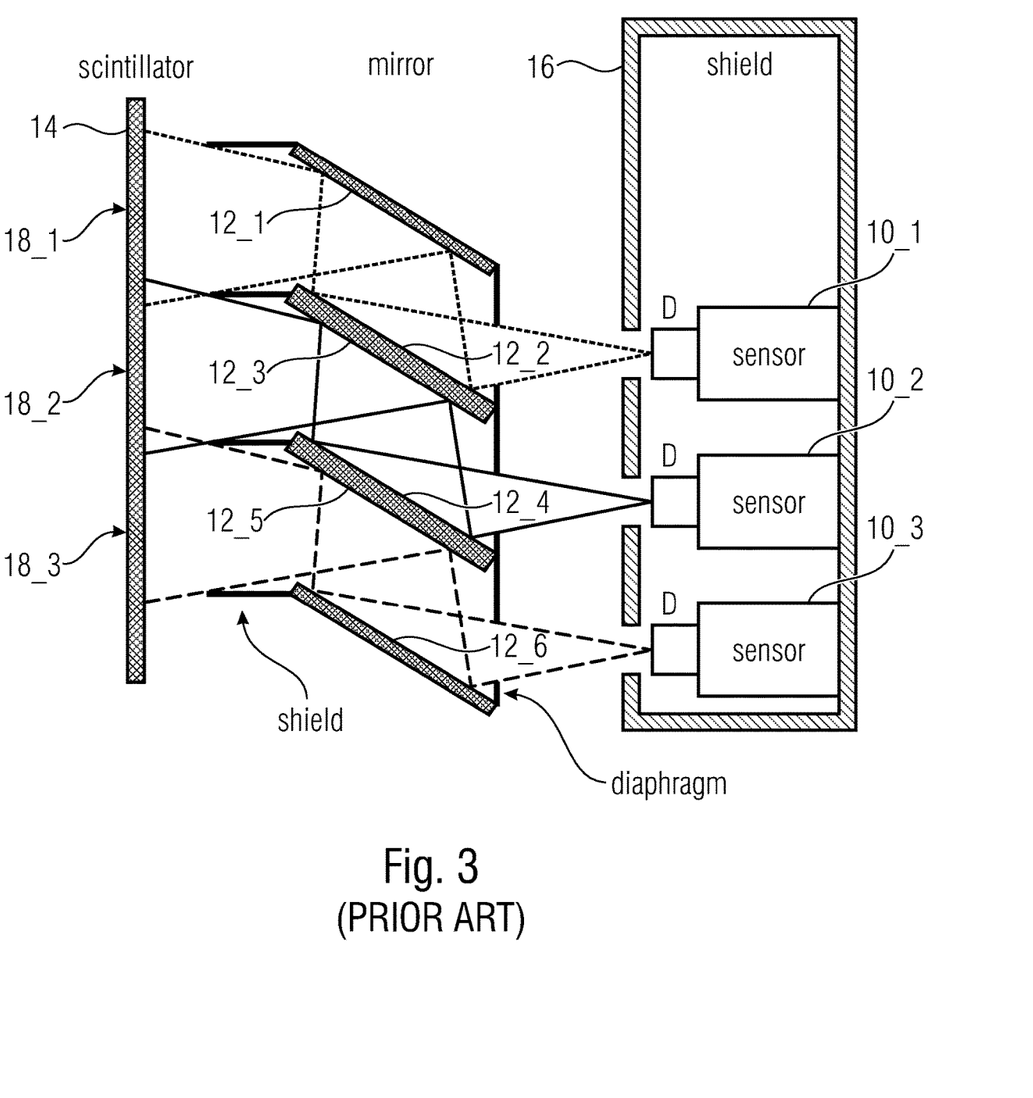
FIG. 3 shows a known mirror/camera arrangement in which three cameras each capture a portion of a scintillator via two respective mirrors.

FIG. 3 shows an example for such a mirror/camera arrangement. Three cameras 10_1 to 10_3 capture a portion 18_1 to 18_3 of the scintillator via two mirrors 12_1 to 12_6, respectively. With respect to the scintillator 14, the cameras 10_1 to 10_3 are arranged such that the capturing directions of the cameras 10_1 to 10_3 are perpendicular to a scintillator plane. Furthermore, the three cameras 10_1 to 10_3 are surrounded by a shield 16 comprising openings in areas adjacent to objectives of the respective cameras 10_1 to 10_3.

Thus, FIG. 3 shows a parallel-mirror arrangement according to the patent of DE 103 01 941, or a mirror/camera arrangement according to the conventional technology. Any number of cameras may be arranged in rows perpendicular to the drawing plane and in a vertical direction.

In order to protect the optical cameras 10_1 and 10_3 from X-radiation that is not absorbed by the scintillator 14 or by the mirrors 12_1 to 12_6, an absorber material (e.g. lead) is located between respectively adjacent mirrors. Furthermore, a special glass is arranged in the optical beam path, which is transparent to visible light but strongly absorbs X-radiation (e.g. lead glass). A further absorber is located between the glasses. Due to the spatial boundary conditions, the distance between respectively adjacent mirrors may not be chosen to be arbitrarily large, which limits the maximum thickness of the lead absorbers respectively used between the mirrors so that the radiation shielding effect is no longer given at very high X-ray energies (e.g. larger than 220 keV or larger than 450 keV).

The above-mentioned disadvantage of the pairwise arrangement of mirrors described in document DE 103 01 941 with regard to shielding against X-radiation penetrating through the scintillator is therefore that the radiation shielding effect is essentially achieved by the absorber material positioned between the two adjacent mirrors. That is, for the usability of a tilable arrangement of optical cameras for imaging a scintillator screen at higher energy, an apparatus may be provided in which the cameras may also be tiled at will, but in which the maximum thickness of the absorber material may be significantly higher.

SUMMARY

According to an embodiment, an image capturing apparatus may have: a screen; a plurality of mirrors; and a plurality of cameras; wherein the plurality of mirrors and the plurality of cameras are arranged such that the plurality of cameras each capture a portion of the screen via a respective one of the plurality of mirrors; and wherein a plurality of cameras is obliquely arranged with respect to the screen; wherein the plurality of cameras is arranged with respect to the screen such that angles between capturing directions of the plurality of cameras and a screen plane are between 5° and 85°.

According to another embodiment, a method for capturing a screen may have the steps of: capturing the screen with a plurality of cameras via a plurality of mirrors; wherein the plurality of mirrors and the plurality of cameras are arranged such that the plurality of cameras each capture a portion of the screen via a respective one of the plurality of mirrors, respectively, and wherein the plurality of cameras is arranged obliquely with respect to the screen; wherein the multitude of cameras is arranged with respect to the screen such that angles between capturing directions of the plurality of cameras and a screen plane are between 5° and 85°.

Another embodiment may have a non-transitory digital storage medium having a computer program stored thereon to perform the method for capturing a screen having the steps of: capturing the screen with a plurality of cameras via a plurality of mirrors; wherein the plurality of mirrors and the plurality of cameras are arranged such that the plurality of cameras each capture a portion of the screen via a respective one of the plurality of mirrors, respectively, and wherein the plurality of cameras is arranged obliquely with respect to the screen; wherein the multitude of cameras is arranged with respect to the screen such that angles between capturing directions of the plurality of cameras and a screen plane are between 5° and 85°, when said computer program is run by a computer.

Embodiments provide an image capturing apparatus comprising a screen, a plurality of mirrors and a plurality of cameras. The plurality of mirrors and the plurality of cameras are arranged such that the plurality of cameras each capture a portion of the screen via a respective one of the plurality of mirrors, wherein the plurality of cameras is arranged obliquely with respect to the screen.

The present invention is based on the idea that, in a tiled arrangement of cameras, a shielding of the cameras may be improved (e. g. by a thicker absorber material between the screen and the camera) without substantially increasing the size of the image capturing apparatus, when the plurality of cameras is arranged obliquely with respect to the screen, and each capture a portion of the screen via one mirror only, respectively.

Further embodiments provide a method. The method includes a step of capturing the screen with a plurality of cameras via a plurality of mirrors, wherein the plurality of mirrors and the plurality of cameras are arranged such that the plurality of cameras each capture a portion of the screen via a respective one of the plurality of mirrors, and wherein the plurality of cameras is arranged obliquely with respect to the screen.

Advantageous implementations may be found in the dependent patent claims.

In embodiments, the plurality of cameras may be arranged obliquely with respect to the screen, i.e., capturing directions of the cameras neither extend in parallel nor perpendicularly to a plane of the screen (screen plane), or to a plane spanned by the screen. For example, the angles between the capturing directions of the plurality of cameras and the screen plane may each be in the range between 5° and 85° (or 10° and 80°, or 15° and 75°, or 20° and 70°, or 25° and 65°, or 30° and 60°).

In embodiments, the plurality of cameras may be arranged such that the capturing directions of the plurality of cameras extend in parallel towards each other.

Furthermore, the plurality of mirrors may be arranged to be tilted with respect to the screen, i. e, mirror planes, or planes of the plurality of mirrors, neither extend in parallel nor perpendicularly to a plane of the screen (screen plane), or to a plane spanned by the screen.

In embodiments, at least one of the plurality of cameras may be (directly or indirectly) arranged behind the screen, i.e., in the direction of radiation impinging on the screen. If the radiation perpendicularly impinges on the screen, the plurality of cameras may be arranged such that a projection of the screen along a screen normal impinges on the at least one of the plurality of cameras.

In embodiments, the apparatus may comprise at least one shielding element arranged between the screen and one of the plurality of cameras such that the at least one of the plurality of cameras is entirely arranged behind the shielding element with respect to the screen. For example, the at least one shielding element (absorber) may be arranged in the direction of the radiation impinging on the screen between the screen and the at least one of the plurality of cameras so that the at least one of the plurality of cameras is protected from radiation passing through the screen.

The at least one shielding element may be arranged outside an optical path extending between the one of the plurality of cameras and the respective portion of the screen via the respective one of the plurality of mirrors. The plurality of cameras, the plurality of mirrors and the at least one shielding element may be arranged such that the optical path of the at least one of the plurality of cameras arranged behind the at least one shielding element passes the at least one shielding element.

In embodiments, the image capturing apparatus may comprise a shield that encloses the plurality of mirrors and the plurality of cameras and that borders at sides of the screen.

The shield may be shaped such that a portion of the shield between the screen and one of the plurality of cameras is arranged such that the one camera is entirely arranged behind the portion of the shield with respect to the screen. At least one other of the plurality of cameras may be arranged behind the at least one shielding element. The portion of the shield and the at least one shielding element may comprise the same or a similar shape. Furthermore, the portion of the shield and the at least one shielding element may be arranged in an equal or similar manner (with respect towards each other, or with respect to the screen or to the respective one of the plurality of cameras).

In embodiments, the image capturing apparatus may comprise a plurality of radiation-protection glasses arranged between the plurality of mirrors and the plurality of cameras. The plurality of radiation-protection glasses may therefore be located in the optical paths between the plurality of mirrors and the plurality of cameras.

In embodiments, the plurality of cameras may each capture the respective portion of the screen via exactly one of the plurality of mirrors. In other words, the number of the mirrors may be equal to a number of the cameras.

In embodiments, the screen may be a scintillator. A scintillator is capable of converting X-radiation into visible light. In detail, when X-radiation (or other high-energy radiation) impinges on the scintillator, the molecules are excited by the scintillator through impact processes, with the scintillator releasing this excitation energy in the form of visible light.

In embodiments, the plurality of mirrors and the plurality of cameras may be arranged such that the plurality of cameras each capture at least partially differing portions of the screen. Thus, the plurality of cameras may be arranged such that the same capture adjacent, or partially overlapping, portions of the screen.

In embodiments, the plurality of cameras may comprise Scheimpflug optics, wherein the plurality of mirrors and the plurality of cameras are arranged such that the plurality of cameras each capture the respective portions of the screen via the respective mirror under Scheimpflug conditions. The Scheimpflug condition is usually used for optically imaging object planes and image planes tilted with respect to each other by means of an objective. The Scheimpflug rule states that the object plane and the image plane have to intersect in a common straight line in order to achieve sharp imaging of the object plane onto an image plane oblique thereto.

In comparison to EP 0 862 748 and DE 103 01 941, embodiments of the present invention provide improved methods/concepts for dividing and imaging the scintillator screen with a fundamentally arbitrary number of optical cameras.

In comparison to EP 0 862 748, the advantage of embodiments of the present invention is that, without increasing the installation depth towards the impinging X-radiation, an arbitrarily large scintillator surface may be divided among a correspondingly large number of optical cameras, and the dimensions of the X-ray camera perpendicular to the beam direction essentially correspond to the size of the scintillator screen to be imaged, whereas in the method described in EP 0 862 748, the dimensions of the X-ray camera are considerably larger than the dimensions of the scintillator screen, since the optical cameras are arranged laterally.

In comparison to DE 103 01 941, the advantage of embodiments of the present invention is that, due to the special optical imaging geometry consisting of mirror/camera arrangement, an absorber with a considerably greater thickness may be used for protection against X-radiation, so that the X-ray detector may be used for a significantly larger X-ray energy range.

BRIEF DESCRIPTION OF THE DRAWINGS

Embodiments of the present invention will be detailed subsequently referring to the ap-pended drawings, in which.

DETAILED DESCRIPTION OF THE INVENTION

In the following description of the embodiments of the invention, the same or equivalent elements are denoted by the same reference numerals so that their description in the different embodiments is interchangeable.

Figure 4:
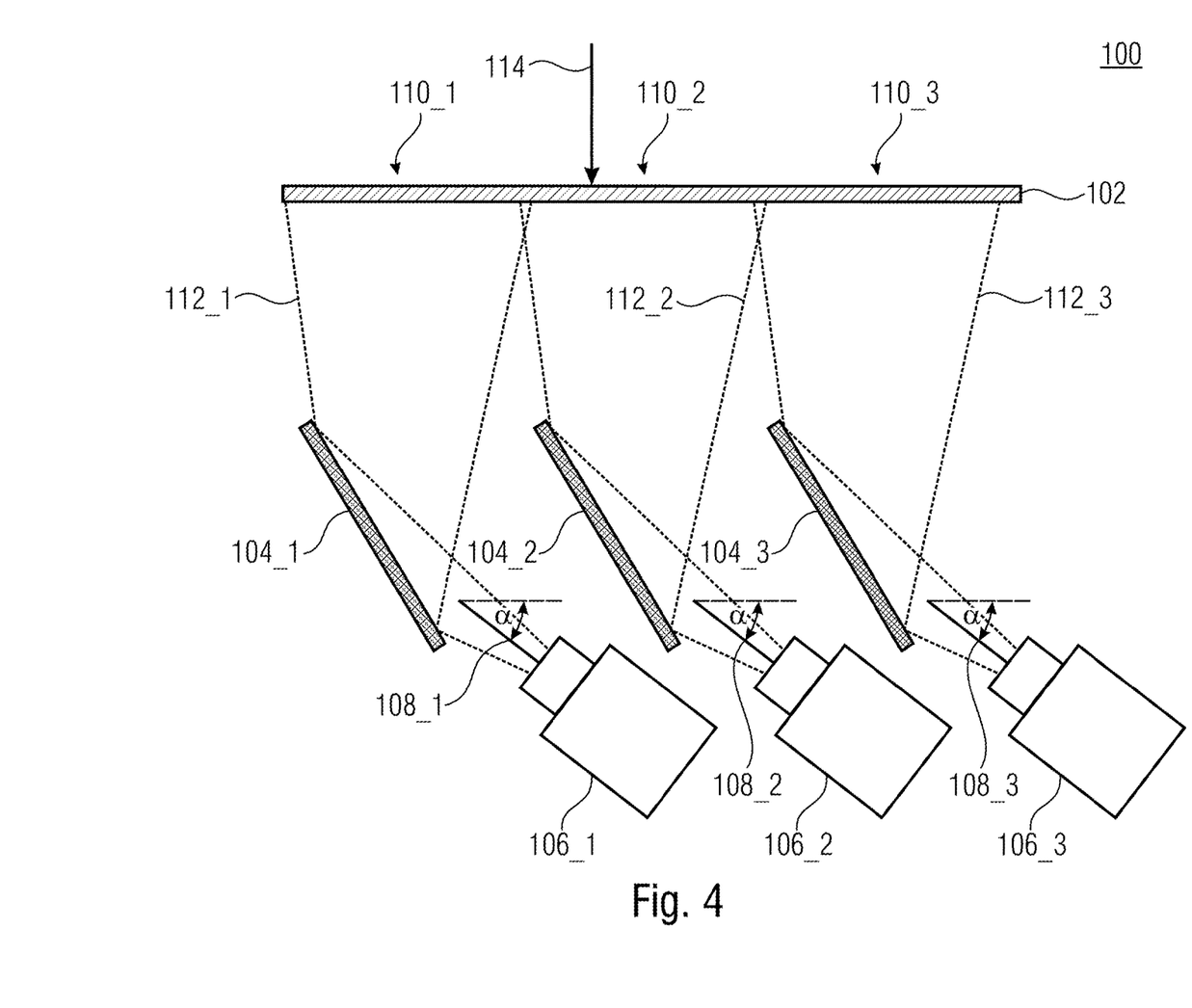
FIG. 4 shows a schematic view of an image capturing apparatus according to an embodiment of the present invention.

FIG. 4 shows a schematic view of an image capturing apparatus 100 according to an embodiment of the present invention. The image capturing apparatus 100 comprises a screen 102, a plurality of mirrors 104_1 to 104_n and a plurality of cameras 106_1 to 106_n (n may be natural number larger than or equal to two, n≥2). The plurality of mirrors 104_1 to 104_n and the plurality of cameras 106_1 to 106_n are arranged such that the plurality of cameras 106_1 to 106_n each capture a portion 108_1 to 108_n of the screen via a respective one of the plurality of mirrors 104_1 to 104_n. The plurality of cameras 106_1 to 106_n is arranged obliquely with respect to the screen 102.

As can be seen in FIG. 4, the plurality of cameras 106_1 to 106_n is arranged obliquely with respect to the screen 102, i.e., capturing directions of the cameras 106_1 to 106_n neither extend in parallel nor perpendicularly to a plane of the screen (screen plane), or to a plane spanned by the screen.

For example, the angles α between the capturing directions (perpendicular to the objective plane) 108_1 to 108_n of the plurality of cameras and of the screen plane may each be in the range between 5° and 85° (or 10° and 80°, or 15° and 75°, or 20° and 70°, or 25° and 65°, or 30° and 60°).

The capturing directions 108_1 to 108_n of the plurality of cameras 106_1 to 106_n may extend in parallel towards each other, i.e., the plurality of cameras 106_1 to 106_n may be arranged at the same angle with respect to the screen.

Furthermore, the plurality of mirrors 104_1 to 104_3 may be arranged to be tilted with respect to the screen, i.e., mirror planes, or planes of the plurality of mirrors 104_1 to 104_3, neither extend in parallel nor perpendicularly to a plane of the screen (screen plane), or to a plane spanned by the screen.

In the following, embodiments of the image capturing apparatus 100 are described in which the image capturing apparatus 100 comprises three mirrors 104_1 to 104_3 and three cameras 106_1 to 106_3. However, the following description may also be accordingly applied to embodiments of the image capturing apparatus 100 in which the image capturing apparatus comprises n mirrors 104_1 to 104_n and n cameras 106_1 to 106_n, wherein n is a natural number larger than or equal to two.

As can be seen in FIG. 4, a first camera 106_1 captures a first portion 110_1 of the screen 102 via a first mirror 104_1, a second camera 106_2 captures a second portion 110_2 of the screen 102 via a second mirror 104_2, and a third camera 106_3 captures a third portion 110_3 of the screen 102 via a third mirror 104_3. Accordingly, a first optical path 112_1 extends between the first camera 106_1 and the first portion 110_1 of the screen 102 via the first mirror 104_1, a second optical path 112_2 extends between the second camera 106_2 and the second portion 110_2 of the screen 102 via the second mirror 104_2, and a third optical path 112_3 extends between the third camera 106_3 and the third portion 110_3 of the screen 102 via the third mirror 104_3.

The three mirrors 104_1 to 104_3 and the three cameras 106_1 to 106_3 may be arranged such that the three cameras 106_1 to 106_3 each capture at least partially differing portions 110_1 to 110_3 of the screen 102, i.e., portions of the screen 102 that are adjacent to each other, or that partially overlap.

Each of the three cameras 106_1 to 106_3 may be assigned exactly one mirror, i.e., each of the three cameras 106_1 to 106_3 captures the respective portion (region) of the screen 102 via exactly one mirror.

The screen 102 may be a scintillator that is configured to convert radiation (e.g. X-radiation) impinging on scintillator into light having a wavelength, or wavelengths, in a range that may be captured by the cameras.

The first camera 106_1 and the second camera 106_2 may be arranged behind the screen 102, or in other words, behind the screen 102 in the direction of the radiation impinging on the screen 102 (indicated by the arrow 114 in FIG. 4). In the case in which the radiation perpendicularly impinges on the screen, a projection of the screen 102 along a screen normal would therefore impinge on the first camera 106_1 and the second camera 106_2.

Figure 5:
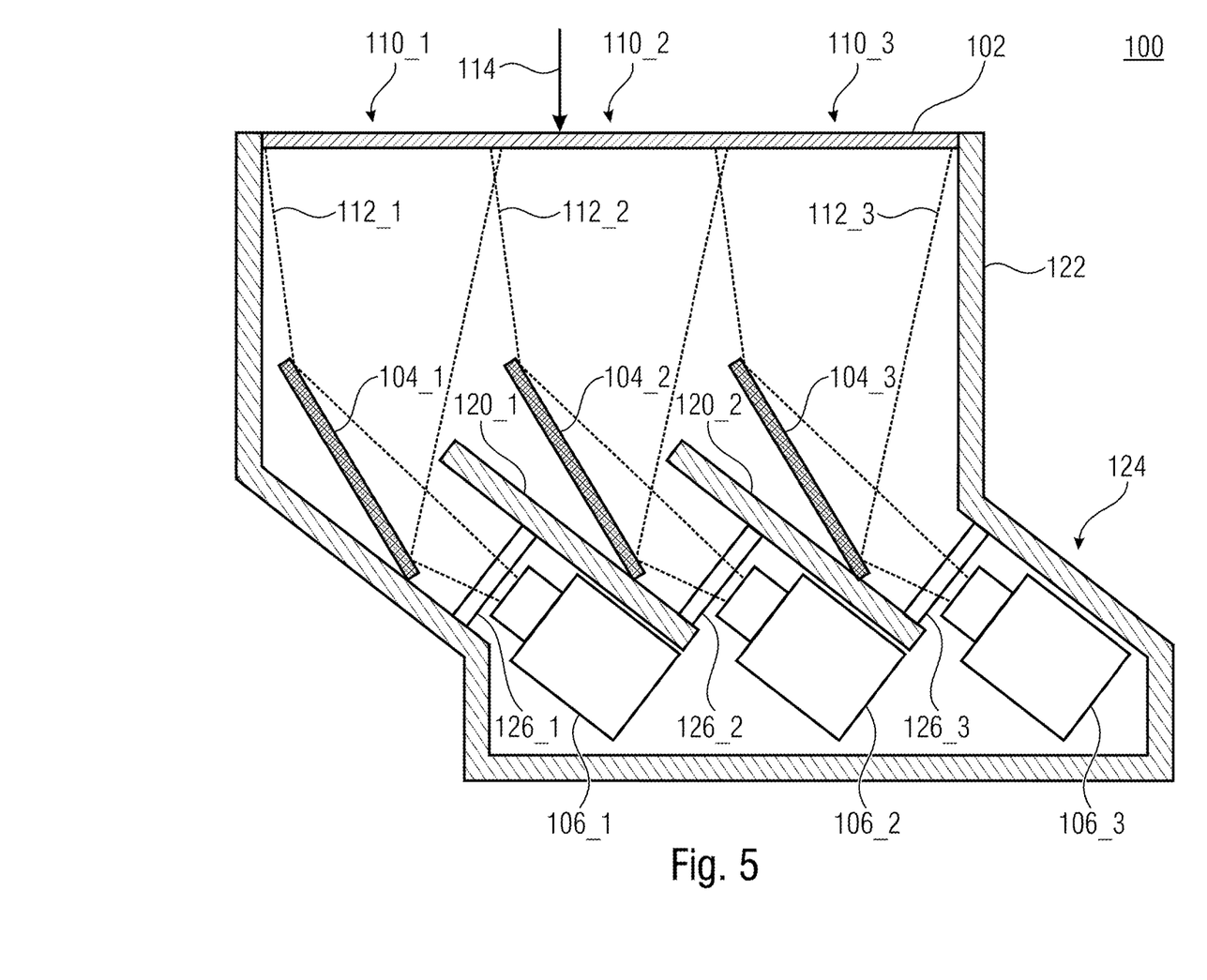
FIG. 5 shows a schematic view of an image capturing apparatus having three obliquely arranged cameras which each capture a portion of the scintillator via exactly one mirror, according to an embodiment of the present invention.
Figure 6:
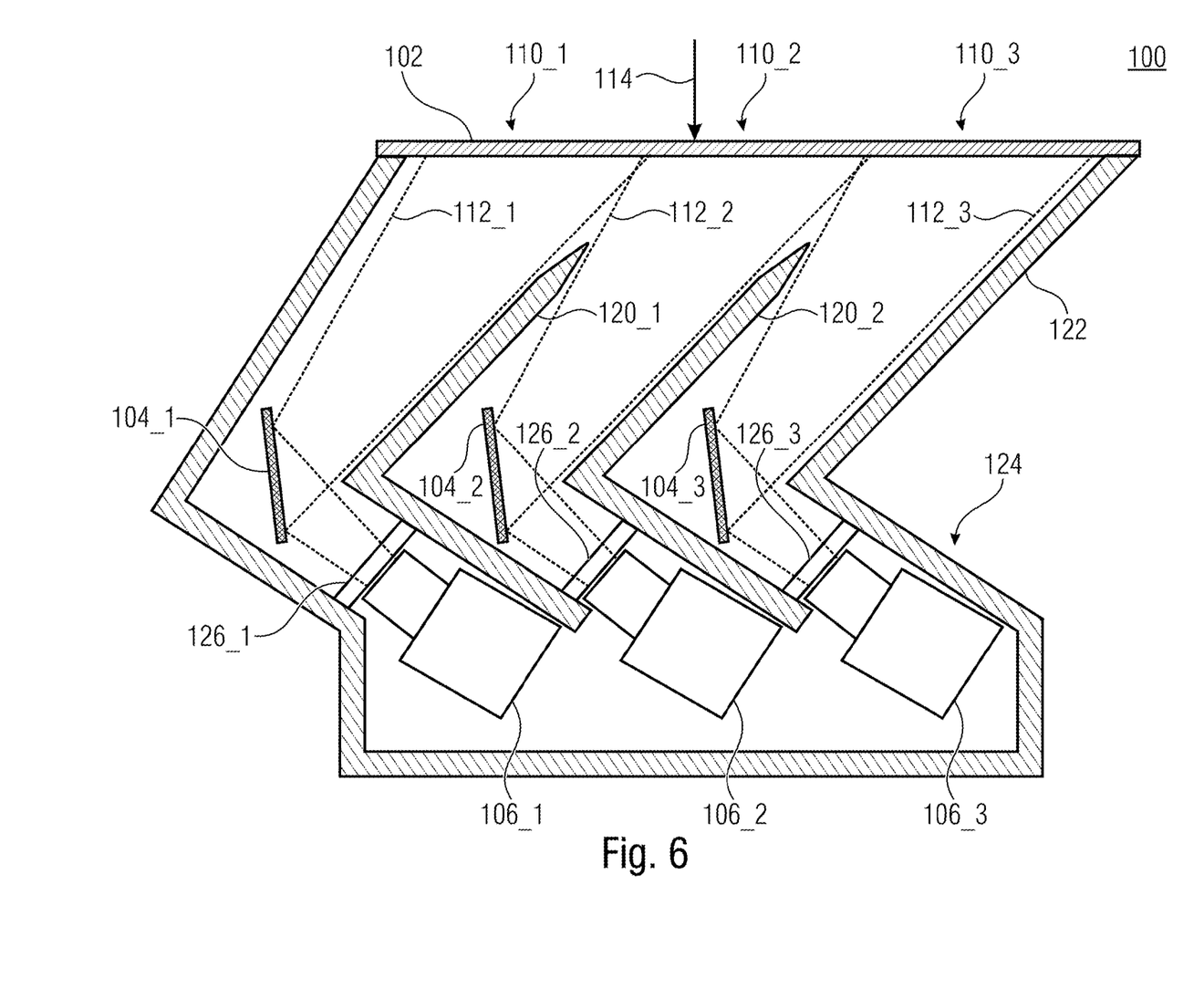
FIG. 6 shows a schematic view of an image capturing apparatus having three cameras which each capture a portion of the scintillator via a respective mirror under Scheimpflug conditions, according to an embodiment of the present invention.

Due to the fact that the cameras 106_1 to 106_3 are arranged obliquely with respect to the screen and capture the respective portion 110_1 to 110_3 of the screen 102 via only one mirror 104_1 to 104_3, respectively, a thicker absorber material may be arranged between the screen 102 and the cameras 106_1 to 106_3 such that a shielding of the cameras 106_1 to 106_3 may be improved without (substantially) increasing an installation size of the image apparatus 100, as is explained in the following based on the embodiments shown in FIG. 5 and FIG. 6.

FIG. 5 shows a schematic view of an image capturing apparatus 100 with three obliquely arranged cameras 106_1 to 106_3, each capturing a portion 110_1 to 110_3 of the scintillator 102 via exactly one mirror 104_1 to 104_3, respectively. In other words, FIG. 5 shows an optical imaging in which the central beams of the camera, or the objectives, extend perpendicularly to a plane of the scintillator. It is to be noted that, although only three cameras are shown in FIG. 5, any number of cameras may be arranged in rows perpendicularly to the drawing plane and in a horizontal direction.

As can be seen in FIG. 5, the image capturing apparatus 100 may comprise a first shielding element 120_1 and a second shielding element 120_2. The first shielding element 120_1 may be arranged between the scintillator 102 and the first camera 106_1 so that the first camera 106_1 is entirely arranged behind the first shielding element 120_1 with respect to the scintillator 102. The second shielding element 120_2 may be arranged between the scintillator 102 and the second camera 106_2 so that the second camera 106_2 is entirely arranged behind the second shielding element 120_2 with respect to the scintillator 102.

For example, the first shielding element (absorber) 120_1 may be arranged between the scintillator 102 and the first camera 106_1 in the direction of the radiation impinging on the scintillator 102 (indicated by the arrow 114 in FIG. 5) so that the first camera 106_1 is protected from radiation (e.g. X-radiation) passing through the scintillator 102. Similarly, the second shielding element (absorber) 120_2 may be arranged between the scintillator 102 and second camera 106_2 in the direction of the radiation impinging on the scintillator 102 so that the second camera 106_2 is protected from radiation (e.g. X-radiation) passing through the scintillator 102.

The first shielding element 120_1 may be configured and arranged such that the same is not located in the first optical path extending between the first camera 106_1 and the first portion 110_1 of the scintillator 102 via the first mirror 104_1. The first optical path 112_1 therefore extends past the first shielding element 120_1, or around the same. Similarly, the second shielding element 120_2 may be configured and arranged such that the same is not located in the second optical path 112_2 extending between the second camera 106_2 and the second portion 110_2 of the scintillator 102 via the second mirror 104_1. Thus, the second optical path 112_2 extends past the second shielding element 120_2, or around the same.

Furthermore, the image capturing apparatus 100 may comprise a shield 122 which encloses and/or includes the three mirrors 104_1 to 104_3 and the cameras 106_1 to 106_3 and borders at sides of the scintillator 102.

The shield 122 may be shaped such that a portion 124 of the shield is arranged between the scintillator and the third camera 106_3 so that the third camera 106_3 is entirely arranged behind the portion 124 of the shield with respect to the scintillator.

The portion 124 of the shield 122 and the shielding elements 120_1 and 120_2 may comprise the same or a similar shape. As can be seen in FIG. 5, the first shielding element 120_1, and the second shielding element 120_2 and the portion 124 of the shield 122 may be I-shaped.

Furthermore, the portion 124 of the shield 122 and the shielding elements 120_1 and 120_2 may be arranged in an equal or similar manner (with respect to each other, or with respect to the scintillator or the respective camera).

Furthermore, the image capturing apparatus 100 may comprise three radiation-protection glasses 126_1 to 126_3.

The first radiation-protection glass 126_1 may be arranged in the first optical path 112_1 between the first camera 106_1 and the first mirror 104_1 such that the first camera is arranged behind the first radiation-protection glass 126_1 with respect to the first optical path 112_1. Furthermore, the first radiation-protection glass 126_1 may be arranged between the first shielding element 120_1 and the first shield 122 such that the first radiation-protection glass 126_1 (entirely) fills out the region between the first shielding element 120_1 and the shield 122.

The second radiation-protection glass 126_2 may be arranged in the second optical path 112_2 between the second camera 106_2 and the second mirror 104_2 such that the second camera is arranged behind the second radiation-protection glass 126_2 with respect to the second optical path 112_2. Furthermore, the second radiation-protection glass 126_2 may be arranged between the first shielding element 120_1 and the second shielding element 120_2 such that the second radiation-protection glass 126_2 (entirely) fills out the region between the first shielding element 120_1 and the second shielding element 120_2.

The third radiation-protection glass 126_3 may be arranged in the third optical path 112_3 between the third camera 106_3 and the third mirror 104_3 such that the third camera 106_3 is arranged behind the third radiation-protection glass 126_3 with respect to the third optical path 112_3. Furthermore, the third radiation-protection glass 126_3 may be arranged between the second shielding element 120_2 and the shield 122 such that the third radiation-protection glass 126_3 (entirely) fills out the region between the second shielding element 120_2 and the shield 122.

FIG. 6 shows a schematic view of an image capturing apparatus 100 comprising three cameras 106_1 to 106_3, each capturing a portion of the scintillator 102 under Scheimpflug conditions via a mirror 104_1 to 104_3, respectively. In other words, FIG. 6 shows an optical imaging under a Scheimpflug condition, i.e., wherein the central beam of the camera extends obliquely to the scintillator. It is to be noted that, although only three cameras are shown in FIG. 6, any number of cameras may be arranged in rows perpendicularly to the drawing plane and in a horizontal direction.

In comparison to the image capturing apparatus shown in FIG. 5, capturing the scintillator 102 is carried out in the image capturing apparatus 100 according to FIG. 6 under a Scheimpflug condition, i.e., wherein the central beam of the camera extends obliquely to the scintillator.

For this, the optics of the three cameras 106_1 to 106_3 are arranged under a Scheimpflug condition. Furthermore, the three mirrors 104_1 to 104_3 and the three cameras 106_1 to 106_3 are arranged such that the three cameras 106_1 to 106_3 capture the respective portions 110_1 to 110_3 of the scintillator via the respective mirrors 104_1 to 104_3 under Scheimpflug conditions (i.e., wherein the central beam of the camera extends obliquely to the scintillator).

The Scheimpflug condition is usually used for optically imaging object planes and image planes tilted towards each other by means of an objective. The Scheimpflug rule states that the object plane, the objective plane and the image plane have to intersect in a common straight line in order to achieve sharp imaging of the object plane onto an image plane perpendicular thereto.

In the case of the "Scheimpflug arrangement", a geometric conversion of the trapezoid-shaped pixels and tiles into a Cartesian system may generally be used, as is explained below, among other things, based on FIG. 7.

With the arrangement of the three cameras 106_1 to 106_3 shown in FIG. 6, it is possible to arrange the three cameras 106_1 to 106_3 behind the scintillator 102, or in other words, behind the scintillator 102 in the direction of the radiation impinging on the screen 102 (indicated by the arrow 114 in FIG. 6). In the case in which the radiation perpendicularly impinges on the scintillator, a projection of the scintillator 102 along a screen normal would therefore impinge on the three cameras 106_1 to 106_3.

Furthermore, with to the arrangement of the three cameras 106_1 to 106_3 shown in FIG. 6, it is possible to enlarge the shielding elements 120_1 and 120_2, e.g., to implement the same in an L-shaped manner, which may further improve shielding the first camera 106_1 and the second camera 106_2. Correspondingly, the portion 124 of the shield may be adapted, whereby shielding the third camera 106_3 may also be improved.

The inventive improvement compared to the apparatus shown in DE 103 01 941 is essentially reached by the fact that the optical imaging of a scintillator by means of a camera module array is realized via individual tilted mirrors and a corresponding oblique position of the camera modules. Shielding the optical cameras and the camera objectives against the X-radiation that is not absorbed in the scintillator may essentially be achieved by introducing between the scintillator and the optical cameras an absorber having a large thickness in the direction of the incident x-radiation. Secondary scattered radiation from the mirror and the absorber may be largely reduced by using a special glass material which is transparent for optical light, but may absorb X-radiation (e.g. lead glass).

In order to realize this arrangement, there are fundamentally two advantageous embodiments, as is explained in the following.

According to a first embodiment, the camera modules may be arranged obliquely, and may each perpendicularly look onto the scintillator via an obliquely positioned mirror (cf. FIG. 5). This has the advantage that the respective camera modules image a rectangular section of the scintillator, so that essentially the regions of the scintillator corresponding to an image element (pixel) are rectangular and in particular square. It should be noted that in this case the mirrors used for the imaging are placed directly in the incoming direction of the incident X-radiation, i.e., radiation not absorbed in the scintillator may fall on the mirrors, which may lead to secondary scattered radiation.

According to a second embodiment, the camera modules may be obliquely arranged and may each view onto the respective scintillator section at an oblique angle via correspondingly titled mirrors (cf. FIG. 6). This has the advantage that the mirrors may also be shielded by additional absorbers from the primary X-radiation such that the resulting secondary scattered radiation is reduced. In this case, the imaged scintillator sections and the pixel sections are isosceles trapezoid-shaped. Furthermore, the pixel resolution on the scintillator does not constantly correspond to the trapezoid-shaped distortion of the scintillator sections. For tiling a multitude of camera modules in both spatial directions of the scintillator, i.e., in a 2-dimensional array, according to the invention it is proposed that the tilt of the viewing direction is realized in an alternating manner between subsequent camera module rows. This has the advantage that the trapezoid-shaped scintillator sections may be joined closely together so that there is no uneven overlapping region between two adjacent module rows. For this case of the imaging of the scintillator and oblique viewing angle, an object-objective-image geometry of the individual camera modules may be realized according to the known Scheimpflug condition so that imaging the scintillator onto the image sensor of the respective camera module which is sharp in the total image region is achieved, which would not be guaranteed without taken the Scheimpflug condition into account. In this case, the Scheimpflug condition is achieved by tilting the normal of the image sensor relative to the optical axis of the image so that the planes of the image sensor, objective and scintillator intersect in a common straight line.

In the present invention, a scintillator screen is imaged onto several optical cameras such that only the visible light originating from the scintillator falls onto the optical cameras, however, X-radiation possibly passing through the scintillator may not cause any radiation damage.

As is shown in FIG. 5 and FIG. 6, the visible light originating from a partial area of the scintillator reaches the optical camera via one mirror, respectively. The camera itself is located behind an absorber made of, e.g., lead or tungsten, so that there is no direct way for the X-radiation to reach the camera.

X-radiation scattered at the mirrors or the absorber may still reach the camera and cause radiation damage, even if the intensity of the scattered X-radiation is significantly lower than the X-radiation incident on the camera. For this reason, a special glass which is transparent for visible light, however, strongly absorbs X-radiation (e.g. lead glass), is arranged at locations where the absorber has to be discontinued for the optical imaging.

By means of additional absorbers above the mirrors, as is shown in FIG. 6, the integral material cross-section of the shield for the optical cameras in the X-radiation direction is further increased so that the detector may be used for significantly higher X-ray energies without radiation damage.

As is shown in FIGS. 4 to 6, the cameras (individual cameras) 106_1 to 106_n may be arranged in an array, wherein each cameras 106_1 to 106_n images a partial area of the screen to be imaged.

Furthermore, the plurality of cameras 106_1 to 106_n may be arranged in a two-dimensional array, wherein each of the cameras 106_1 to 106_n images a partial area of the screen to be imaged, wherein the partial areas may overlap.

Each of the plurality of cameras 106_1 to 106_n may deliver an individual image of the respective partial area of the screen to be imaged.

In embodiments, the digital frames of the plurality of cameras 106_1 to 106_n may be corrected at a resolution that is higher than the resolution that the optical image of the camera is finally supposed to have. Thus, the cameras 106_1 to 106_n may both provide a high light sensitivity and at the same time deliver output images that are suitable for automatic image processing. On the one hand, this concept is advantageous in that normally available individual cameras may be arranged in an array without having to make certain modifications to the cameras, for example, to reduce the resolution. The array of individual images obtained by the individual cameras may then be subjected to correction processing at a higher resolution as is already obtained by using conventional individual cameras, in order to adjust the individual images obtained by the individual cameras to each other and, if applicable, eliminate any overlapping regions. From the result of the correction, including a possibly present elimination of overlapping regions, a total image having a resolution used for the correction may be obtained, which is higher than the resolution ultimately involved. This total image having a high resolution may well have edges at the borders of the individual partial images.

For edge reduction and resolution reduction, post-processing of the total image may then be carried out in such a way that adjacent pixels are combined with each other, for example, by addition. The number of pixels combined with each other depends on the ratio of the correction resolution to the ultimately involved total resolution and may vary from case to case. However, the combination of adjacent pixels after the correction results in the edges still visible in the high resolution image becoming invisible at the transition from one frame to another, resulting in a total image with a desired total resolution, which is easy to handle in its data volume, and which has no or only barely visible edges at the border from one partial image to the next partial image. The ultimately obtained total image is thus well-suited for subsequent image processing due to the freedom of edges on the one hand and the reduced amount of data on the other.

As the individual cameras 106_1 to 106_n, cameras may be used which allow the possibility of so-called "binning", e.g. CCD cameras. For example, with CCD cameras, a type of analog charge addition of adjacent rows and columns may be performed before or during the read-out of the CCD sensor, which is particularly favorable because this addition is not affected by electronic noise which would occur if the binning was performed digitally after read-out and analog/digital conversion.

Such a digital combination of adjacent pixels may only be performed after applying the correction rules for the individual images in order to achieve the final resolution reduction and edge elimination.

Thus, conventional small-area CCD cameras with a lens optic that is only slightly reduced in size may be used so that two sensitivity advantages are achieved compared to using a single CCD camera with a strongly reduced lens optic. On the one hand, the loss of light will be considerably lower in the slightly reduced lens optic as compared to the strongly reduced lens optic. On the other hand, an additional sensitivity advantage is obtained by analog binning, or the digital combination of adjacent pixels after correction.

Since CCD sensors or even CMOS image sensors may be used, image repetition frequencies for large-area capturing are possible, which are up to a factor of 1000 higher than the repetition frequencies that may be achieved with amorphous silicon detectors for similar image formats.

Specific correction rules may be used for each individual camera 106_1 to 106_n in order to correct, or adjust, the individual images. However, these correction rules only have to be determined once, for example, before delivery of the camera, and remain the same if the adjustment of the individual cameras is not changed. Such correction rules, for example in the form of lookup tables, etc., may easily be hard-wired and, generally speaking, may be carried out very efficiently, for example by means of a DSP, since they are only simple pixel shifts/sortings which are unproblematic with regard to the computing effort involved.

As already mentioned, the cameras 106_1 to 106_n may be placed in the optical path of the X-rays behind the scintillator layer 102 in order to be able to use short-focal length objectives that are available with a higher light intensity than the long-focal length objectives otherwise involved. Such long-focal length objectives are needed if a camera is not placed in the optical path of the X-radiation, but using mirror optics outside the X-rays in order to protect the optical camera from the X-rays.

In order to protect the cameras against X-rays passing through the scintillator screen, additionally protection discs 126_1 to 126_n, e.g. made of lead glass, may be used which may further be implemented to be heatable to counteract interferences of the lead glass due to X-rays, in particular stronger X-radiation.

Figure 7:
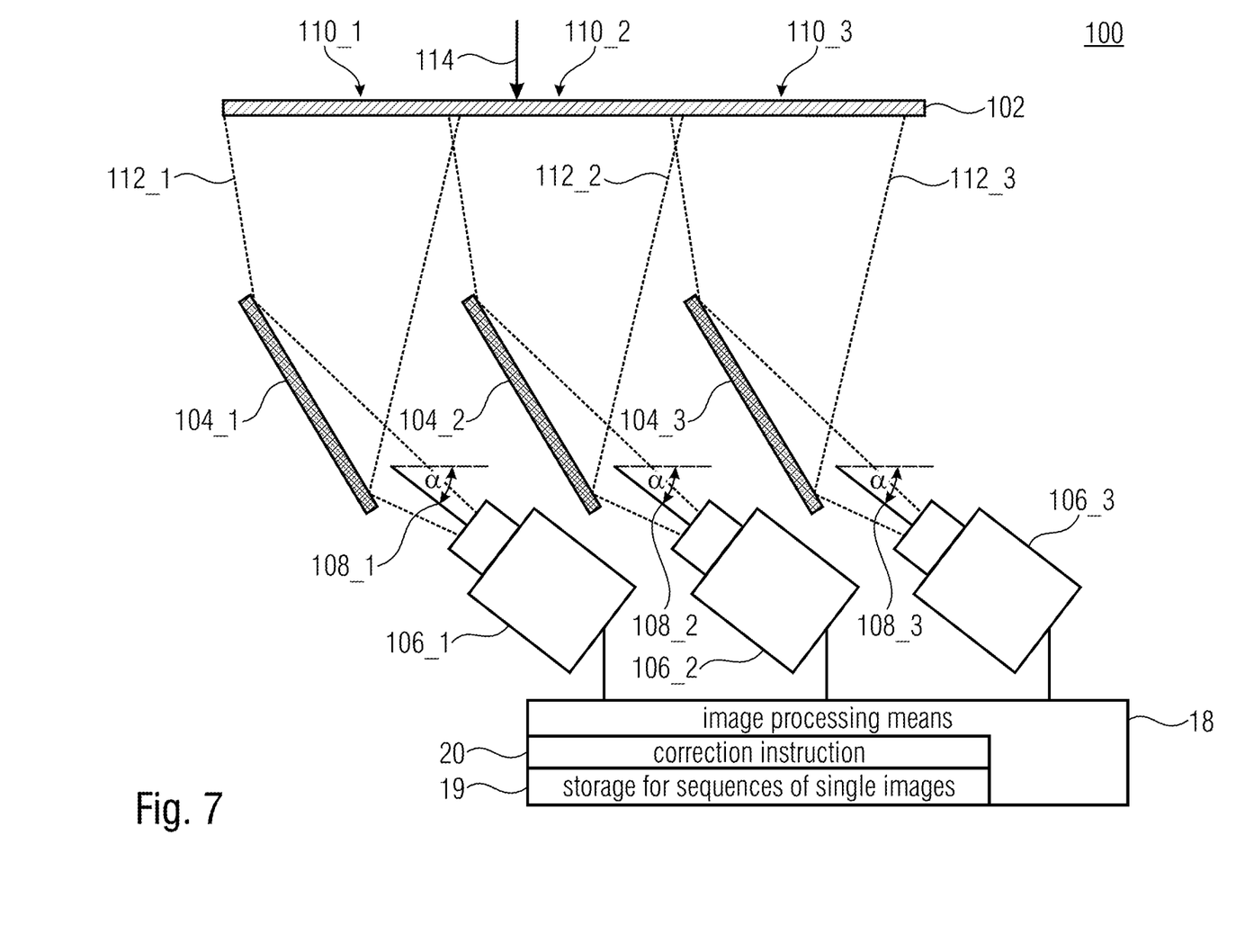
FIG. 7 shows a schematic view of an image capturing apparatus according to an embodiment of the present invention.

FIG. 7 shows a schematic view of an image capturing apparatus 100 according to an embodiment. Compared to the image capturing apparatus 100 shown in FIG. 4, the image capturing apparatus 100 shown in FIG. 7 additionally comprises an image processing means 18 for processing the digital individual images of the array of optical individual cameras 106_1 to 106_n, wherein the image processing means 18 is configured to generate the optical image of the screen 102 with the predetermined total resolution.

As mentioned above, a predetermined total resolution may be provided for the optical capturing of the screen 102, wherein each of the plurality of cameras 106_1 to 106_n may be configured to capture the respective portion of the screen 102, which includes a partial area of the screen surface, with an individual resolution that is higher than the total resolution.

The image processing means 18 may be configured to melt the individual images of the plurality of cameras into a total image that represents the optical capturing of the screen with the predetermined total resolution.

Furthermore, the image processing means 18 may be configured to compute each pixel of the total image by summing up in a weighted manner locally corresponding pixels of the individual images.

The weighted summing may be carried out in two stages, for example, wherein pixels of the individual images are first combined to a high-resolution total image and, subsequently, binning into the total resolution is performed. Alternatively, the weighted summing up may also be carried out in one stage.

The locally corresponding pixels of the individual images may be pixels of the individual images that consider or result in the respective pixel of the total image.

By reducing the resolution, the low-pass filter effect may be reduced. Furthermore, it is possible to correct distortions, positional errors, sensitivity deviations of the imaging sensors of the plurality of cameras and meltings of the edge regions of the plurality of cameras.

As described above, capturing directions of the cameras 106_1 to 106_n may essentially extend in parallel to each other. However, it has to be taken into account that the capturing directions of the cameras 106_1 to 106_n may slightly deviate from each other, or differ from each other, due to tolerances (e.g. assembly tolerances, or orientation tolerances of the cameras 106_1 to 106_n, or manufacturing tolerances of the cameras 106_1 to 106_n). These deviations may also be corrected by the image processing means.

Furthermore, the image processing means 18 may be operable to carry out a correction on the digital individual images in order to reduce or completely eliminate orientation inaccuracies and/or parameter deviations in the array of individual optical cameras 106_1 to 106_n. In order to correct an individual image, a correction rule 20 is used that is determined in a calibration preceding capturing, which is typically stored in the image processing means 18 on a suitable storage medium or is even hard-wired. The correction with the correction rule determined in the calibration may be carried out at a correction resolution which is higher than the predetermined total resolution of the total optical capturing that is ultimately desired, and which is lower than or equal to the individual resolution with which the optical individual cameras 106_1 to 106_n deliver the individual images. Finally, the image processing means 18 may be operable to obtain corrected individual images or a corrected total image. Combining the individual images to the total image may therefore be carried out after the correction of the individual images with the correction rule 20 determined for each individual image, i.e. for each individual camera 106_1 to 106_n, before the final pixel combination step or after the final pixel combination step. However, due to reasons of efficiency and quality, it is advantageous to first combine the total image with the high optical resolution after the correction of the individual images and then add adjacent pixels based on the combined total image in order to obtain the optical capturing with the predetermined total resolution. The final step of the combination of adjacent pixels is therefore executed in order to bring the total image, which is present with the high-correction resolution, to the lower desired predetermined total resolution. This final step has the advantage that, since it is already carried out with corrected individual images, possible artefacts at the boundaries of the corrected individual images are blurred and therefore made unrecognizable, and that a resolution reduction is further carried out in order to not obtain any total image having a resolution that is too high. Images having a resolution that is too high are not particularly manageable for further processing due to their high amount of data. In addition, an extremely high resolution is not required for many applications so that a resolution reduction may be readily carried out.

Embodiments take advantage of the fact that by using several cameras 106_1 to 106_n, the available image elements (pixels) grow proportionally to the number of cameras 106_1 to 106_n. Often, however, as it has been explained, a pixel number is involved that is not larger than which would be provided by an individual camera, as will be explained in following example.

If, for example, four optical cameras are used, four pixels may be added together in this case. This is particularly advantageous if the charge may already be added together on the sensor, as takes place with CCD sensors through so-called binning. In this case, the charge has to be read-out electronically only once and thus the electronic noise generated by this process is generated only once, so that the overall signal-to-noise ratio is better than if each pixel is read-out individually and added digitally. In the present exemplary case of the 4×4 situation, the correction may take place either at the highest resolution, i.e. without binning having been performed. Alternatively, a 2×2 binning could exemplarily be carried out in order to carry out the correction at a fourfold resolution with regard to the desirable total resolution. In this case, a final resolution reduction step by digitally combining adjacent pixels, e.g. by addition, would be possible, wherein 2×2 pixels, i.e. four adjacent pixels, are combined every time according to a certain combination rule which may either combine in an overlapping manner or in an adjacent manner or achieves a pixel combination of adjacent pixels in any other manner. Thus, an optimally accurate correction at a high resolution is possible and at the same time, due to the resolution reduction after the correction, a suppression of artefacts due to single image edges is achieved.

As can be seen in FIG. 7, the array of cameras 106_1 to 106_n may be located behind the scintillator screen 102, wherein each of the cameras 106_1 to 106_n images a part of the scintillator screen 102, respectively. For special tasks where a line camera is usually used, the array of individual optical cameras 106_1 to 106_n degenerates into a one-dimensional array including a linear arrangement of optical individual cameras. The regions imaged by the individual optical cameras may either be directly adjacent or may slightly overlap in order to reduce the adjustment effort typically involved on mechanical side.

If the partial images, or individual images, have an overlap, an electronic correction may be performed. If the partial images overlap, in particular the area imaged in both cameras 106_1 to 106_n is discarded after the read-out of the individual optical cameras 106_1 to 106_n, and the optical total capturing, after the correction that also includes discarding the overlap region, is combined of the corrected individual images that were subjected to discarding, and is resolution-reduced.

Although embodiments have been described above in which the cameras 106_1 to 106_n are arranged in a two-dimensional grid which is congruent to a grid according to which the portions, or partial areas of the screen, captured by the cameras are arranged, it is to be noted that this is not required. Instead, the cameras 106_1 to 106_n may also be arranged in a two-dimensional grid which is not congruent to a grid according to which the portions, or partial areas of the screen, captured by the camera are arranged.

Figure 8:
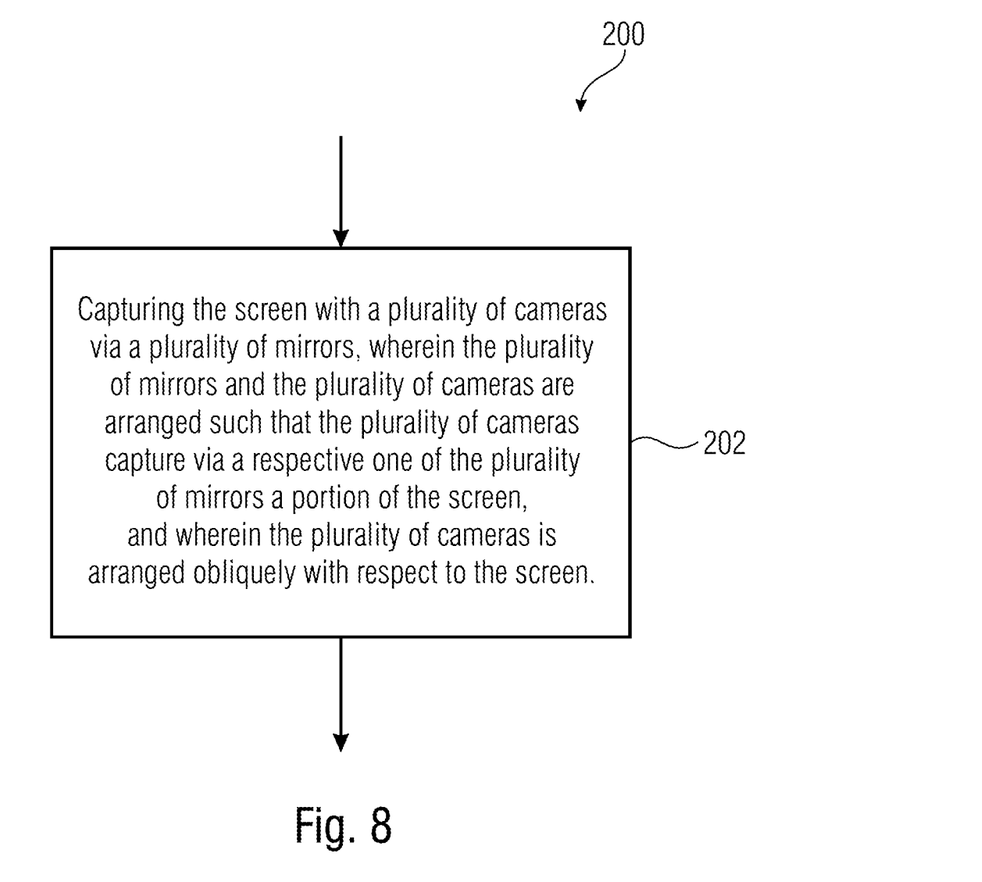
FIG. 8 shows a flow diagram of a method for capturing a screen according to an embodiment.

FIG. 8 shows a flow diagram of a method 200 for capturing a screen. The method 200 includes a step 202 of capturing the screen with a plurality of cameras via a plurality of mirrors, wherein the plurality of mirrors and the plurality of cameras are arranged such that the plurality of cameras each capture a portion of the screen via a respective one of the plurality of mirrors, and wherein the plurality of cameras is arranged obliquely with respect to the screen.

Further embodiments provide an apparatus for imaging a screen (scintillator) by means of a multitude of camera modules, characterized in that the imaging is achieved by stringing together camera modules which are obliquely arranged and look onto the screen via a correspondingly tilted mirror.

In the further embodiments, a thick radiation-absorbing material (absorber) may be attached between the scintillator and the cameras so that a radiation-protection effect may be achieved at high X-ray energies (e.g. >200 keV, or >450 keV).

In the further embodiments, imaging the scintillator may take place in parallel to the normal of the scintillator. A central beam of the optical path between the respective portion of the screen and the respective mirror may therefore extend in parallel to the normal of the screen.

In the further embodiments, imaging the scintillator may take place obliquely to the normal of the scintillator. A central beam of the optical path between the respective portion of the screen and the respective mirror may therefore extend obliquely to the normal of the screen.

In the further embodiments, a sharp imaging of the scintillator may be achieved by means of a Scheimpflug condition.

In the further embodiments, a radiation-absorbing glass may be introduced between the mirror and the objective.

Even though some aspects have been described within the context of a device, it is understood that said aspects also represent a description of the corresponding method, so that a block or a structural component of a device is also to be understood as a corresponding method step or as a feature of a method step. By analogy therewith, aspects that have been described within the context of or as a method step also represent a description of a corresponding block or detail or feature of a corresponding device. Some or all of the method steps may be performed while using a hardware device, such as a microprocessor, a programmable computer or an electronic circuit. In some embodiments, some or several of the most important method steps may be performed by such a device.

Depending on specific implementation requirements, embodiments of the invention may be implemented in hardware or in software. Implementation may be effected while using a digital storage medium, for example a floppy disc, a DVD, a Blu-ray disc, a CD, a ROM, a PROM, an EPROM, an EEPROM or a FLASH memory, a hard disc or any other magnetic or optical memory which has electronically readable control signals stored thereon which may cooperate, or cooperate, with a programmable computer system such that the respective method is performed. This is why the digital storage medium may be computer-readable.

Some embodiments in accordance with the invention thus comprise a data carrier which comprises electronically readable control signals that are capable of cooperating with a programmable computer system such that any of the methods described herein is performed.

Generally, embodiments of the present invention may be implemented as a computer program product having a program code, the program code being effective to perform any of the methods when the computer program product runs on a computer.

The program code may also be stored on a machine-readable carrier, for example.

Other embodiments include the computer program for performing any of the methods described herein, said computer program being stored on a machine-readable carrier.

In other words, an embodiment of the inventive method thus is a computer program which has a program code for performing any of the methods described herein, when the computer program runs on a computer. The data carrier, the digital storage medium, or the recorded medium are typically tangible, or non-volatile.

A further embodiment of the inventive methods thus is a data carrier (or a digital storage medium or a computer-readable medium) on which the computer program for performing any of the methods described herein is recorded.

A further embodiment of the inventive method thus is a data stream or a sequence of signals representing the computer program for performing any of the methods described herein. The data stream or the sequence of signals may be configured, for example, to be transferred via a data communication link, for example via the internet.

A further embodiment includes a processing means, for example a computer or a programmable logic device, configured or adapted to perform any of the methods described herein.

A further embodiment includes a computer on which the computer program for performing any of the methods described herein is installed.

A further embodiment in accordance with the invention includes a device or a system configured to transmit a computer program for performing at least one of the methods described herein to a receiver. The transmission may be electronic or optical, for example. The receiver may be a computer, a mobile device, a memory device or a similar device, for example. The device or the system may include a file server for transmitting the computer program to the receiver, for example.

In some embodiments, a programmable logic device (for example a field-programmable gate array, an FPGA) may be used for performing some or all of the functionalities of the methods described herein. In some embodiments, a field-programmable gate array may cooperate with a microprocessor to perform any of the methods described herein. Generally, the methods are performed, in some embodiments, by any hardware device. Said hardware device may be any universally applicable hardware such as a computer processor (CPU), or may be a hardware specific to the method, such as an ASIC.

The above-described devices may, for example, be implemented using a hardware apparatus, or using a computer, or using a combination of a hardware apparatus and a computer.

The above-described devices or any components of the above-described devices may at least be partially implemented in a hardware and/or software (computer program).

The above-described methods may, for example, be implemented using a hardware apparatus, or using a computer, or using a combination of a hardware apparatus and a computer.

The above-described methods or any components of the above-described methods may at least be partially implemented in a hardware and/or software (computer program).

The above-described embodiments merely represent an illustration of the principles of the present invention. It is understood that other persons skilled in the art will appreciate modifications and variations of the arrangements and details described herein. This is why it is intended that the invention be limited only by the scope of the following claims rather than by the specific details that have been presented herein by means of the description and the discussion of the embodiments.

The invention claimed is:

1. An image capturing apparatus, comprising:
a screen;
a plurality of mirrors; and
a plurality of cameras;
wherein the plurality of mirrors and the plurality of cameras are arranged such that the plurality of cameras each capture a portion of the screen via a respective one of the plurality of mirrors; and wherein the plurality of cameras is obliquely arranged with respect to the screen;
wherein the plurality of cameras is arranged with respect to the screen such that angles between capturing directions of the plurality of cameras and a screen plane are between 5° and 85°;
wherein the screen is a scintillator screen,
wherein the capturing directions are perpendicular to objective planes of the plurality of cameras.

2. The image capturing apparatus according to claim 1, wherein the plurality of cameras is arranged such that the capturing directions of the plurality of cameras extend in parallel to each other.

3. The image capturing apparatus according to 1, wherein at least one of the plurality of cameras is arranged behind the screen.

4. The image capturing apparatus according to claim 1, wherein the image capturing apparatus comprises at least one shielding element arranged between the screen and one of the plurality of cameras so that the at least one of the plurality of cameras is entirely arranged behind the shielding element with respect to the screen.

5. The image capturing apparatus according to claim 4, wherein the at least one shielding element is arranged outside an optical path extending between the one of the plurality of cameras and the respective portion of the screen via the respective one of the plurality of mirrors.

6. The image capturing apparatus according to claim 4, wherein the at least one shielding element is configured to absorb X-ray energy of 200 keV or more.

7. The image capturing apparatus according to claim 6, wherein the at least one shielding element is L-shaped.

8. The image capturing apparatus according to claim 6, wherein the at least one shielding element is I-shaped.

9. The image capturing apparatus according to claim 1, wherein the image capturing apparatus comprises a shield enclosing the plurality of mirrors and the plurality of cameras and bordering at sides of the screen.

10. The image capturing apparatus according to claim 9, wherein the shield is shaped such that a portion of the shield is arranged between the screen and one of the plurality of cameras so that the one of the plurality of cameras is entirely arranged behind the portion of the shield with respect to the screen.

11. The image capturing apparatus according to claim 10, wherein the image capturing apparatus comprises at least one shielding element arranged between the screen and one of the plurality of cameras so that the at least one of the plurality of cameras is entirely arranged behind the shielding element with respect to the screen, wherein the at least one shielding element is configured to absorb X-ray energy of 200 keV or more, wherein at least one other of the plurality of cameras is arranged behind the at least one shielding element.

12. The image capturing apparatus according to claim 1, wherein the image capturing apparatus comprises a plurality of radiation-protection glasses arranged between the plurality of mirrors and the plurality of cameras.

13. The image capturing apparatus according to claim 1, wherein the plurality of cameras captures the respective portion of the screen via exactly one of the multitude of mirrors, respectively.

14. The image capturing apparatus according to claim 1, wherein a number of the mirrors is equal to a number of the cameras.

15. The image capturing apparatus according to claim 1, wherein the screen is a scintillator.

16. The image capturing apparatus according to claim 1, wherein the plurality of mirrors and a plurality of cameras are arranged such that the plurality of cameras captures at least partially differing portions of the screen.

17. The image capturing apparatus according to claim 1, wherein the plurality of camera/optic combinations comprises a Scheimpflug arrangement;
wherein the plurality of mirrors and the plurality of cameras are arranged such that the plurality of cameras each captures the respective portion of the screen under Scheimpflug conditions via the respective mirrors.

18. The image capturing apparatus according to claim 1, wherein imaging the screen takes place in parallel to a normal of the screen.

19. The image capturing apparatus according to claim 1, wherein imaging the screen takes place obliquely to a normal of the screen.

20. The image capturing apparatus according to claim 1, wherein the screen comprises an area, and wherein a predetermined total resolution is provided for the optical capturing of the screen, wherein each of the plurality of cameras is configured to capture the respective portion of the screen, which comprises a partial area of the screen area, with an individual resolution that is higher than the total resolution.

21. The image capturing apparatus according to claim 20, wherein the image capturing apparatus comprises an image processor for processing individual images of the plurality of cameras, wherein the image processor is configured to melt the individual images of the plurality of cameras into a total image that represents the optical capturing of the screen with the predetermined total resolution.

22. The image capturing apparatus according to claim 21, wherein the image processor is configured to compute each pixel of the total image by weighted summing up of locally corresponding pixels of the digital individual images.

23. A method for capturing a screen, comprising:
capturing the screen with a plurality of cameras via a plurality of mirrors;
wherein the plurality of mirrors and the plurality of cameras are arranged such that the plurality of cameras each capture a portion of the screen via a respective one of the plurality of mirrors, respectively, and
wherein the plurality of cameras is arranged obliquely with respect to the screen;
wherein the multitude of cameras is arranged with respect to the screen such that angles between capturing directions of the plurality of cameras and a screen plane are between 5° and 85°;
wherein the screen is a scintillator screen,
wherein the capturing directions are perpendicular to objective planes of the plurality of cameras.

24. A non-transitory digital storage medium having a computer program stored thereon to perform the method for capturing a screen, comprising:
capturing the screen with a plurality of cameras via a plurality of mirrors;
wherein the plurality of mirrors and the plurality of cameras are arranged such that the plurality of cameras each capture a portion of the screen via a respective one of the plurality of mirrors, respectively, and
wherein the plurality of cameras is arranged obliquely with respect to the screen;
wherein the multitude of cameras is arranged with respect to the screen such that angles between capturing directions of the plurality of cameras and a screen plane are between 5° and 85°;
wherein the screen is a scintillator screen, wherein the capturing directions are perpendicular to objective planes of the plurality of cameras,
when said computer program is run by a computer.

\* \* \* \* \*